US005486454A

United States Patent [19]
Madonna et al.

[11] Patent Number: 5,486,454
[45] Date of Patent: Jan. 23, 1996

[54] NUCLEIC ACID PROBE FOR THE DETECTION OF SALMONELLA HUMAN PATHOGENS

[75] Inventors: M. Jane Madonna, Middlesex; Derek Woods, Flemington, both of N.J.

[73] Assignee: Ortho Diagnostic Systems, Inc., New Brunswick, N.J.

[21] Appl. No.: 243,749

[22] Filed: May 17, 1994

Related U.S. Application Data

[63] Continuation of Ser. No. 26,256, Mar. 4, 1993, abandoned, which is a continuation of Ser. No. 672,743, Mar. 21, 1991, abandoned, which is a continuation of Ser. No. 309,441, Feb. 13, 1989, abandoned.

[51] Int. Cl.$^6$ .............................. C12Q 1/68; C07H 21/04
[52] U.S. Cl. ............................................ 435/6; 536/24.32
[58] Field of Search ................................ 435/6; 536/24.32

[56] References Cited

U.S. PATENT DOCUMENTS

| | | | |
|---|---|---|---|
| 4,358,535 | 11/1982 | Falkow et al. | 435/5 |
| 4,458,066 | 7/1984 | Caruthers et al. | 536/27 |
| 4,486,539 | 12/1984 | Ranki et al. | 436/504 |
| 4,533,628 | 8/1985 | Mass | 435/6 |
| 4,556,643 | 12/1985 | Paau et al. | 436/501 |
| 4,563,419 | 1/1986 | Ranki et al. | 435/6 |
| 4,623,618 | 11/1986 | Rokugawa | 435/6 |
| 4,689,295 | 8/1987 | Taber et al. | 536/27 |
| 4,717,653 | 1/1988 | Webster, Jr. | 435/6 |
| 4,816,389 | 3/1989 | Sansonetti et al. | 436/501 |
| 4,851,331 | 7/1989 | Vary et al. | 935/77 |

FOREIGN PATENT DOCUMENTS

| | | |
|---|---|---|
| 0114668 | 1/1984 | European Pat. Off. . |
| WO83/01459 | 4/1983 | WIPO . |
| WO87/03911 | 7/1987 | WIPO . |

OTHER PUBLICATIONS

Webster's II New Riverside Dictionary, Houghton Mifflin, Boston, 1984, p. 26.
Purcell et al. J. Bact. 169:5831–5834 (1987).
Anslanzedah, Jand Paulissen, L. J., Abstracts for the Annual Meeting of the American Society For Microbiology, Abstract #B–119, 87th Annual Meeting, Atlanta, Ga. (1987).
Armarnath et al., Chemical Synthesis of Oligonucleotides, Chemical Reviews, vol. 77, No. 2, pp. 183–217 (1977).
Broker et al., Electron Microscopic Visualization of tRNA Genes with Ferritin–Avidin: Biotin Labels, Abs., Nuc Acids Res, vol. 5, No. 2, pp. 363–384 (1978).
Clegg et al., Enterobacterial Fimbriae, Journal of Bacteriology, vol. 169, No. 3, pp. 934–938 (1987).
Crichton et al., J. Med. Microbiol., vol. 32, pp. 145–152 (1990).
Crichton et al., J. of Appl. Bacteriology, vol. 67, pp. 283–291.

European Patent Office Search Report for Application Ser. No. EP 90 03 1440.
Farmer et al., the Salmonella–Arizona Group of Enterobacteriaceae: Nomenclature, Classification and Rpting, Clin. Microbio. Newsltr, vol. 6, No. 9, pp. 63–66 (1984).
Feutrier et al., J. Bacteriology, vol. 170, pp. 4216–4222 (1988).
Langer et al., Enzymatic Synthesis of Biotin–Labeled Polynucleotides: Novel Nuc Acid Affinity Probes, Proc Natl Acad Sci USA, vol. 78, No. 11, pp. 6633–6637 (1981).
Manning et al., A New Method of In Situ Hybridization, Chromosoma, vol. 53, pp. 107–117 (1975).
Manning et al., A Method for Gene Enrichment based on the Avidin–Biotin Interaction, Biochemistry, vol. 16, No. 7, pp. 1364–1360 (1977).
Moseley et al., Detection of Enterotoxigenic *Escherichia coli* by DNA Colony Hybridization, Jour. of Infectious Diseases, vol. 142, No. 6., pp. 892–898 (1980).
Nichols et al., Nucleotide Sequences of trpA of *Salmonella Typhimurium* and *Escherichia coli*, Proc Natl Acad Sci USA, vol. 76, No. 10, pp. 5244–5248 (1979).
Sodja et al., Gene Mapping and Gene Enrichment by the Avidin–Biotin Interaction, Abstract, Nucleic Acids Reserach, vol. 5, No. 2, pp. 385–401 (1978).
Stoleru et al., Polynucleotide Sequence Divergence Among Strains of Salmonella Sub–Genus IV and Closely Related Organisms, Ann Microbiol, vol. 127, pp. 477–486 (1976).
van der Ploeg, Hybridocytochemistry with Non–radioactive Probes as a Tool for Biomedical Research, Folia Hist. Et Cytobio. vol. 24, No. 3, pp. 189–194 (1986).
Textbook of Biochemistry with Clinical Correlations, p. 842, T. M. Devlin, ed., John Wiley & Sons, New York, N.Y. (1982).
Hames et al., eds., *Nucleic Acid Hybridization*, Chapter 2, Washington: IRL Press, 1985.
Maniatis et al., *Molecular Cloning*, Cold Spring Harbor Laboratory, 1982.
Marmur et al., *Molecular Basis of Neoplasia*, University of Texas Press, 1962.
Ploeg, Folia Histochemica et Cytobiologica, 24:189–194, 1986.
Stoleru et al., Chem. Abstracts, 85:80053b, 1976.

Primary Examiner—Stephanie W. Zitomer
Attorney, Agent, or Firm—Woodcock Washburn Kurtz Mackiewicz & Norris

[57] ABSTRACT

Nucleic acid probes that detect Salmonella human pathogens are generated from the nucleotide sequences of a gene encoding a virulence factor involved in the pathogenesis of Salmonella, especially the Type 1 fimbriae protein. Preferred probe lengths are about 20 to about 100 nucleotide bases. The probes are highly specific and sensitive for detecting Salmonella organisms pathogenic to humans and are thus clinically useful in the detection of infection in diarrhea specimens. They also may be used in the detection of food-borne Salmonella, the causative agent of most salmonellosis in humans.

22 Claims, No Drawings

NUCLEIC ACID PROBE FOR THE DETECTION OF SALMONELLA HUMAN PATHOGENS

CROSS REFERENCE TO RELATED APPLICATIONS

This application is a continuation application of U.S. Ser. No. 08/026,256, filed Mar. 4, 1993, abandoned, which is a continuation application of U.S. Ser. No. 07/672,743, filed Mar. 21, 1991, abandoned, which is a continuation application of U.S. Ser. No. 07/309,441, filed Feb. 13, 1989, abandoned.

FIELD OF THE INVENTION

Described herein are nucleic acid probes that can detect Salmonella human pathogens. The probes are generated from the nucleotide sequence of a gene encoding a protein factor involved in the pathogenesis of Salmonella, especially the Type 1 fimbrial protein.

BACKGROUND OF THE INVENTION

Microorganisms from the genus Salmonella are responsible for the majority of cases of bacterial diarrhea occurring in humans. Typically, screening and identification of a Salmonella infection is accomplished by microbial culturing techniques followed by biochemical testing. This takes from one to three days, sometimes ending in equivocal results. Identification of Salmonella spp. by use of an assay using DNA probes would be less labor intensive for the clinician, provide unequivocal results, and would enable quicker diagnosis of salmonellosis.

Nucleic acid hybridization technology is a new approach in the diagnostic industry. This methodology exploits the property that sequences unique to an organism comprise its genome. In a hybridization test, a positive signal is generated when these unique genomic sequences in the bacterial or the viral target hybridize with nucleic acid probes, which are tagged with a detection label. U.S. Pat. No. 4,689,295 to Taber, et al. describes Salmonella DNA probes which are Salmonella DNA fragments common to more than 80% of the known Salmonella species. The fragments do not code for any protein or any other material known to contribute to pathogenicity. Thus, the probes are constructed from a library of fragments without regard to genetic function, and are principally used to detect the presence of Salmonella in a food sample.

U.S. Pat. No. 4,358,535 to Falkow, et al. describes a method for detecting microorganisms using a DNA probe by affixing the genetic material from a sample containing the microorganism to an inert support and treating the sample to render the genetic material in a single-stranded form. The fixed material is then contacted with a labeled nucleotide sequence that is substantially complementary to a nucleotide sequence of a structural gene encoding for toxins produced by the microorganisms. E. coli is the only organism exemplified in the patent, although Salmonella is mentioned in a laundry list of toxin-producing microorganisms.

U.S. Pat. Nos. 4,486,539 and 4,563,419 to Ranki, et al. describe a one-step sandwich hybridization technique employing reagents having distinct single-stranded nucleic acid fragments isolated from the genome of a microbe to be identified. These fragments have no extensive sequence homology but are situated closely together in the genome. There is no mention of specific genes encoding for a proteinaceous virulence factor that may be involved in human pathogenicity from infection with a microbe from the genus Salmonella.

Nichols and Yanofsky, Proc. Natl. Acad. Sci., Vol. 76, No. 10, pp. 5244–5248 (October 1979) describe the nucleotide sequences of trpA of *Salmonella typhimurium* and *Escherichia coli* and make an evolutionary comparison of the two. There is no mention of using these sequences as DNA probes.

Stoleru, et al., Chem. Abstracts, 85:90053b (1976) describe polynucleotide divergence among strains of Salmonella sub-genus IV and other closely related organisms. Here again, there is no mention of using sequences for DNA probes.

DETAILED DESCRIPTION OF THE INVENTION

The nucleic acid probes of the invention are believed to be unique to nucleic acid from microorganisms of the genus Salmonella causing human pathogenicity, especially those belonging to Subgroups 1, 2, 3a, and 3b, 4, and 6 of that genus, as that classification is reported by the Center for Disease Control in Atlanta, Ga. (see *Clinical Microbiology Newsletter*, Vol. 6, No. 9, pp. 63–66, for a discussion of Salmonella Classification). Importantly, the probes are unique to nucleic acid from those microorganisms belonging to Subgroups 1, 3a, and 3b, which encompass almost all the Salmonella human pathogens. They are thus capable of hybridizing by way of complementary base pair binding to a nucleic acid sequence from Salmonella that contains at least some complementarity, termed a "target sequence". The sequences can be either RNA or DNA. It should be understood that this binding of the probe of the invention to the target sequence does not have to be perfectly matched. There may, in fact, be unpaired regions resulting in interior loops, bulge loops, hairpin loops, cruciform binding or any other mismatched regions. The key point is that hybridization must occur to the extent necessary to allow detection of the target sequence.

The nucleic acid probes of the invention are also believed to correspond to certain nucleic acid sequences that encode proteins, which proteins may be referred to as virulence factors, involved in the pathogenesis of human disease caused by Salmonella microorganisms, especially the fimbrial-type proteins, otherwise known as the pili. Of these proteins that may be involved in one way or another with the pathogenesis of Salmonella infection may be mentioned Type 1 fimbriae proteins, Type II fimbriae proteins, Type III fimbriae proteins, and the like, with the Type 1 fimbriae proteins being the most notable.

Fimbriae are straight and rigid appendages extending from a bacterial cell. In the case of enteric microorganisms, they have been implicated in the life cycle of the organism (Clegg, S. and G. F. Gerbach, J. Bacteriol. 169:934–938 (1987). Although for most microorganisms the role of fimbriae has not yet been clearly elucidated, for *E. coli*, fimbriae aid in bacterial *E. coli* colonization of the human or animal host, a phenomenon necessary for infection. Clegg and co-workers (supra at 934) report that only bacteria identified as *E. coli* or belonging to the genus Shigella demonstrate genetic sequences involved in fimbrial expression. However, other workers have suggested that Type 1 fimbriae may be involved in the adherence and pathogenosis of *Salmonella enteritidis* (Jaber Anslanzedah and Leo J. Paulissen, Jewish Hospital of St. Louis, Mo., Abstracts of the Annual Meeting of the American Society for Microbiology, Abs. #B119, 87th Annual Meeting, Atlanta, Ga., March 1987).

The length of the nucleic acid sequences in the probes of the invention is a length which is sufficient to allow hybridization to occur to at least a portion of the DNA from Salmonella, whether chromosomal or plasmid borne, but preferably chromosomal DNA, to allow detection of said DNA. Surprisingly, however, relatively shorter lengths have demonstrated a specific, high affinity binding, enabling easy detection of target nucleic acid. Accordingly, preferred for use herein, are probes having a nucleic acid sequence of about 20 to about 400 nucleotide bases long. It is more preferred that said sequences be about 20 to 200 bases long, most preferably about 20 to about 100 bases long.

In the preferred embodiments, the probe comprises a nucleic acid sequence having at least about 20 nucleotide bases comprising in whole or in part the following sequence:

```
5'-ATGAGACATAAATTAATGACCTCTACTATTGCGAGTCTGATGTTTGTCGCTGCCGCA
GCGGTTGCGGCTGATCCTACTCCGGTGAGCGTGGTGGGCGGGACTATTCATTTCGAAGGT
AAACTGGTTAATGCAGCCTGTGCCGTCAGCACTAAATCCGCCGATCAAACGGTGACGCTG
GGTCAATACCGTACCGCCAGCTTTACGGCGATTGGTAATACGACTGCGCAGGTGCCTTTC
TCCATCGTCCTGAATGACTGCGATCCGAAAGTGGCGGCCACCGCTGCCGTGGCTTTCTCT
GGTCAGGCAGATAACACCACCCCTAATTTGCTGGCTGTGTCCTCTGCGGACAATAGCACT
ACCGCAACCGGCGTCGGGATTGAGATTCTTGATAATACCTCTTCACCGTTGAAGCCGGAC
GGCGCGACCTTCTCGGCGAAGCAGTCGCTGGTTGAAGGCACCAATACGCTGCGTTTTACC
GCACGCTATAAGGCAACCGCCGCCGCCACGACGCCAGGCCAGGCTAATGCCGACGCCACC
TTTATCATGAAATACGAATAA-3'
```

In more preferred embodiments, the nucleotide probe comprises all or a portion of at least one of the following sequences, or all or a portion of a sequence complementary thereto, said sequences selected from the group consisting essentially of:
5' . . . CAGGCCAGGCTAATGCCGACGCCACCTT-TATCATGAAATACGAATAAT . . . 3',
5' . . . CCTACTCCGGTGAGCGTGAGTGGCGG-TACTATTCATTTCGAAGGTAAACT . . . 3',
5' GCG TGC GGT AAA ACG CAG CGT ATT GGT GCC TTC AAC-3',
5' TAG TGC TAT TGT CCG CAG AGG AGA CAG CCA-3',
5' GCC GGT TGC GGT AGT GCT ATT GTC CGC AGA-3',
5' ACC CAG CGT CAC CGT TTG ATC GGC GGA TTT-3',
5' GTA TTG GTG CCT TCA ACC AGC GAC TGC TTC-3',
5'-ATT GCG AGT CTG ATG TTT G-3',
5'-TGC AGC CTG TGC CGT CAG C-3',
5'-TCT GCG GAC AAT AGC ACT A-3',
5'-GTT GAA GGC ACC AAT AC-3',
5'-TGC CGT TCC CTG ACG GGA-3',
5'-GCG TGC GGT AAA ACG CAG-3',
5'-CCC GAC GCC GGT TGC GG-3',
5'-GGC CGC CAC TTT CGG AT-3',
5'-GTT TGA TCG GCG GAT TT-3', and
5'-GCT CAC CGG AGT AGG ATC -3'.

In the most preferred embodiments, the nucleic acid probes comprise all or a portion of at least one of the following sequences, or all or a portion of sequences complementary thereto:
5' GCCGGTTGCGGTAGTGCTATTGTCCGCAGA 3', and
5' GTATTGGTGCCTTCAACCAGCGACTGCTTC 3'.

It should be appreciated that any part of the sequences detailed above, having a length of at least about 20 nucleotide bases, and being capable of hybridizing to the nucleic acid of Salmonella, especially chromosomal DNA, is within the contemplation of the present invention. For example, a sequence of nucleic acid which begins in the middle of one of above-described sequences and extends further than the end of that sequence, and which detects Salmonella appreciable cross-hybridization with other species, is suitable for use in the invention. Overlapping sequences, combinations of smaller subsequences found within the sequences described above, and the like, are also included. Additional sequences that do not interfere with the hybridization abilities of the probe are also included, such as primer sequences, cloning site sequences, and any other type of flanking sequence.

As alluded to, DNA sequences complementary to those specifically depicted above are also suitable for use in the invention. In vivo, DNA exists as a double helix with complementary strands. DNA hybridization methods which utilize the probes of the invention break apart the double strands to provide single-stranded chromosomal DNA which is then available to bind with the probe. The probes of the invention bind to one strand of the denatured double-stranded target DNA, whereas the complementary sequence of the probe would bind to the other strand.

Subsets, derivatives, subclones and mutations of the nucleotide sequences as detailed above, which do not detract from the ability of the nucleotide sequences to detect Salmonella, are also suitable for use in the invention. As used herein, the terms "subsets" means nucleotide sequences having fewer than the entire number of nucleotides in a discrete nucleotide sequence. As used herein, the term "derivatives" means discrete nucleotide sequences of the invention having additional oligonucleotides not derived from Salmonella. These may be purposely attached, such as polynucleotide sequence that may be termed a tail, or other sequences interspersed throughout the sequences taught herein which are not completely complementary to specific portions of the nucleic acid from Salmonella, but do not interfere with the overall ability of the probe to hybridize to the nucleic acid of Salmonella.

As used herein, the term "subclones38 means fragments of the original nucleic acid sequences as taught herein, which have been inserted into a vector. It is well known in the art that subsets, derivatives, subclones and mutations of nucleotide sequences may function in the same way as the original nucleotide sequence.

The nucleic acid probes of the invention are labeled to signal hybridization to target nucleic acid from a microorganism belonging to the genus Salmonella. The labeling may take on many forms, including conventional radioisotopic labeling, chemical labeling, immunogenic labeling, or a label with light scattering effect, and the like. Suitable methods to detect such labels are scintillation counting, autoradiography, fluorescence measurement, colorimetric measurement, or light emission measurement.

Thus, the labeling may comprise a radiolabel (e.g. $^{14}C$, $^{32}P$, $^{3}H$, and the like), an enzyme (e.g., horseradish peroxidase, alkaline or acid phosphatase, and the like), a bacterial label, a fluorescent label, an antibody (which may be used in a double antibody system), an antigen (to be used with a labeled antibody), a small molecule such as biotin (to be used with an avidin, streptavidin, or antibiotin system), a latex particle (to be used in a buoyancy or latex agglutination system), an electron dense compound such as ferritin) to be used with electron microscopy), or a light scattering particle such as colloidal gold, or any combinations or permutations of the foregoing.

For example, if the labeling portion of the probe is an antigen, a signal can be generated by complexing said antigen with an antibody/enzyme conjugate, followed by an addition of an enzyme substrate. If this portion were an antibody, signal can be generated by complexing anti-antibody or an $F_C$ binding protein such as Protein A therewith, when such second antibody or Protein A have been conjugated to an enzyme.

For reasons of ease and safety in the handling of the probe, it is preferred that it be chemically labeled, especially enzymatically or immunologically. In more preferred embodiments, the chemical label of choice is a hapten such as biotin, iminobiotin, fluorescein, and the like.

Among the preferred labeling systems that may be mentioned are those based on the biotin/streptavidin system. This system can be incorporated into the probe by a variety of means. For example, the probe can be covalently attached to biotin via a cytochrome c bridge (Manning, etal., Biochemistry, 16: 1364–1370 (1977), Manning, et al., Chromosoma, 53: 107–117 (1975), Sodja, A., Nucleic Acids Research, 5: 385–401 (1978)), or the biotin can be covalently incorporated into specific nucleotide residues (Langer, P. R., Proceedings of one National Academy of Sciences, USA, 78: 6633–6637 (1981), or the biotin can be attached to a polynucleotide by means of a diamine (e.g., pentane diamine) bridge (Broker, T. R., et al., Nucleic Acids Research 5: 363–384 (1978)). Interaction of the biotin molecules is accomplished with avidin, streptavidin or antibiotin antibodies that are conjugated to such signalling components as latex particles (Sodja, A., et al, supra, or Manning, et al. Chromosoma, supra,) ferritin (Broker, supra, a fluorogen such as fluorescein, an enzyme, secondary antibodies, magnetic particles, or the like.

In some preferred embodiments, however, the chemical label is attached to a "tail sequence" which is affixed to the 3' terminal end of the probe. The tail sequence of the nucleic acid probes of the invention are preferably composed of nucleotide bases. In more preferred embodiments of the invention, the nucleotides are adenosine and uridine. In the most preferred embodiments of the invention the tail sequence has a composition of approximately 90% adenosine and 10% uridine. The nucleotide sequence of the tail is preferably approximately 200 to 400 bases long. The tail sequence may be added to the probe by enzymatic reaction using terminal deoxynucleotidyl transferase (Pharmacia), or by any other conventional method.

The nucleic acid sequences useful in the nucleic acid probes of the invention are readily prepared by any conventional method such as organic synthesis, recombinant DNA techniques or isolation from genomic DNA, especially that DNA that carries a fim gene, which encodes for a fimbrial protein. However, the sequences as described herein are particularly amenable to organic synthesis using techniques known in the art, such as techniques utilizing a nucleic acid synthesizer and commercially available reagents.

Accordingly, then, the probes of the present invention are preferably made synthetically rather than being derived from genomic DNA or RNA. Methods of chemically synthesizing the oligonucleotide probes of the present invention are well known in the art. One such method is the phosphoramidite method described in U.S. Pat. No. 4,458,066 (Caruthers, et al.). Other methods are described in V. Amarnath et al. (1977), Chem. Rev. 77: 183–217. Since the preferred probes of the present invention are relatively short, they therefore can be efficiently made by an automated DNA synthesizer. The probes may also conveniently be tailed with additional nucleotides, for example, biotin labeled nucleotides, preferably less than about 1000 bases, more preferably about 150 to about 500 bases, most preferably about 200–400 bases. Chemical synthesis of the probes makes it possible to easily produce large numbers of purified probes with specific nucleotide sequences rather than relying on the difficult recombinant procedures of isolating and purifying the genetic information from a natural source.

The probes may be provided in a lyophilized form, to be reconstituted in a buffer appropriate for conducting hybridization reactions. Alternatively, the probes may already be present in such a buffer or reagent solution, providing a reagent for detection of human pathogenic Salmonella. Such a reagent solution comprises agents that, in general, enhance the ability of the probe to bind to the target nucleic acid. For example, the reagent solution may contain any suitable hybridization enhancer, detergent, carrier DNA, and a compound to increase the specificity, such as formamide. Such a reagent solution may comprise one or more nucleotide sequences as described herein, in any combination, as the probe portion of the reagent. In the preferred embodiments, the reagent solution comprises formamide, especially in the amounts of about 40% to about 60% of buffer volume, more preferably about 47% to about 55%. In the particularly preferred embodiments, the reagent solution also contains a carrier DNA.

The use of the probes as described herein is not limited to any specific method or technique of conducting hybridization to the nucleic acid in a biological specimen, to detect the target sequence. Several hybridization assay techniques are known to the art and include, for example, dot blot hybridization, Southern blotting; sandwich hybridization assays such as those described by Ranki, et al., in U.S. Pat. Nos. 4,563,415 and 4,486,539; sandwich hybridization on beads as described by Hansen, et al. in European Patent Application 84306513.7; displacement hybridization techniques such as those described in WO 87/03911; capture techniques wherein the nucleic acid probes as described herein are first immobilized onto a solid support and then contacted with sample; in situ hybridization such as those cited or described by Ploeg, Folia Histochemica et Cytobiologica, Vol. 24 (1986) No. 3, pp 189–194; and the like.

The target analyte polynucleotide of a microorganism belonging to the genus Salmonella, may be present in various media, most often in a biological, physiological, or environmental specimen. It is preferred in some cases to subject the specimen containing the target polynucleotide to a variety of extraction, purification, and isolation protocols before conducting analysis according to the methods of this invention. Measures such as these are desirable to rid the sample of substances that might interfere with binding of the analyte to the hybridization probe. Examples of such protocols may be found in the second chapter of *Nucleic Acid Hybridization*, ed. B. Hames & S. Higgins, IRL Press, Washington, D.C. (1985), and in standard textbooks.

It is also within the contemplation of the present invention that synthetic homo- or hereto-polynucleotides can be prepared in the laboratory to serve as the target analyte despite their abiological origins, as such synthetic polynucleotides might be desirable for research in the area of the pathogenesis of Salmonella infection, and the like.

Additionally, sample containing target analyte nucleotide sequences must often be treated to convert any target analyte to single-stranded form. This conversion to single-stranded form may be accomplished by a variety of ways conventional to the art. For example, the denaturation of duplex nucleic acids can be accomplished thermally, chemically or in other conventional ways. The denaturation process will depend upon the pH, ionic strength, temperature, and other properties of the ambient medium (e.g., presence of urea, formamide, glyoxal, methyl mercury hydroxide or other agents), as well as upon the base composition (i.e., the GC/AT ratio), sequence, and length of the duplex nucleic acid. Reviews of various methods of denaturation may be found in standard textbooks, and in J. Marmur, C. Schildkraut and P. Doty in *Molecular Basis of Neoplasia*, Univ. of Texas Press, Austin, Tex., 1962; and T. Maniatis, E. F. Fritsch, and J. Sambrook, in *Molecular Cloning*, Cold Spring Harbor Laboratory, 1982.

Exemplary of a hybridization reaction are situations wherein the target analyte nucleotide is provided in a liquid medium. This medium may take many forms, most illustrative of which is unprocessed biological fluid, or solid biological samples dispersed in water or other compatible liquid medium. The unprocessed biological fluid can be mixed with a "second solution" in some embodiments so as to produce a medium known to support rehybridization of complementary single-stranded nucleic acids.

The second solution may be aqueous or nonaqueous or a mixture of both. Certain inorganic or organic additives known to affect rehybridization of complementary single-stranded nucleic acids may be added to enhance the rate of hybridization and/or to increase the equilibrium extent of rehybridization (i.e., stability of the rehybridized form). Of the inorganic additives may be mentioned sodium citrate and sodium chloride; of the organic compounds may be mentioned such compounds as formamide. Other useful additives are polyethylene glycol, dextran sulfate, sodium dodecyl sulfate and casein.

The probe may be contacted with a liquid sample under conditions in which the analyte target nucleotide sequence, if present, can hybridize in whole or in part to a complementary region contained in the target recognition moiety of the probe nucleotide. This contacting step may be effectuated in a variety of ways, and under varying conditions of "stringency". A review of factors which affect rehybridization (reassociation) processes is available in *Nucleic Acid Hybridization*, ed. B. Hames and S. Higgins, IRL Press, Washington, D.C. (1985). The factors include conditions of temperature, pH, salt concentration and solvent medium, in addition to factors which reflect the length, complexity, and degree of complementarity of the probe and analyte target polynucleotides. The contact period may vary depending on the length of time necessary to effect hybridization to the desired extent, which is dependent in part on the length of the binding region in the target recognition moiety as well as the reaction conditions.

The nucleotide probe, with any bound complementary target analyte, is separated from the biological sample after the desired hybridization has taken place. This separation may be accomplished by any suitable procedure including, but not limited to chromatography (column, gel, etc.), filtration, electrophoresis (including electroelution) and the like. It may be further desirable to incorporate a rinsing step to ensure that unbound material is fully separated from rehybridized material which has bound to the probe.

Once the hybridization event has taken place and the bound material is separated from unbound, detection of the label on the probe is undertaken by assaying the bound material, unbound material, or both. If the label is a radioactive one, direct detection can be accomplished through conventional radioisotopic quantitation techniques. If the label is a chemical one, as for example, biotin, indirect detection takes place.

The following are more specific examples of certain embodiments of the present invention, but are not to be considered limitative thereof.

EXAMPLES

Example 1—Testing a Double-Stranded "fim" Probe

A double stranded DNA probe was derived from the chimeric plasmid pISC137 (Purcell, B., et al., Journal of Bacteriology, Volume 169, pp. 5831–5834 (1987)) A 1.6 Kb EcoRI-HpaI fragment carrying the fim gene from S. typhimurium was $^{32}$P-labeled and used in hybridization experiments to test specificity and sensitivity of the fim probe. Both ATCC strains and clinical isolates were examined for reactivity with the probe in dot blot experiments (Table 1). It appeared that the fim gene could act as a novel probe for Salmonella.

TABLE I

| Hybridization Pattern of fim Probe | | |
|---|---|---|
| Target Organism | | Hybridization Signal |
| S. choleraesuis | ATCC#13312 | + |
| S. enteriditis | ATCC#13076 | + |
| S. typhi | ATCC#6539 | + |
| S. typhimuruim | ATCC#14028 | + |
| S. typhimuruim | ATCC#19585 | + |
| S. typhimuruim | Clinical isolate | + |
| Shigella boydiae | ATCC#9207 | − |
| S. dysenteriae | ATCC#29026 | − |
| S. sonnei | ATCC#11060 | − |
| S. flexneri | ATCC#12022 | − |
| E. coli | ATCC#9339 | − |
| E. coli | ATCC#25922 | − |
| E. coli | ATCC#9546 | − |
| Campylobacter jejuni | ATCC#29428 | − |
| C. jejuni | ATCC#33560 | − |
| C. fecalis | ATCC#33709 | − |
| C. coli | ATCC#33559 | − |
| Pseudomonas aeruginosa | ATCC#27853 | − |
| Klebsiella pneumoniae | ATCC#13583 | − |
| Bacillus | | − |

A positive hybridization signal was seen after autoradiography if the $^{32}$P-labeled probe reacted with target DNA.

Example 2—Use Of Synthetic Oligonucleotides as Probes

Starting with the DNA sequence of the entire fim gene, 5' to 3':

5'-AT GAGACAT AAATT AAT GACCT CT ACT ATT GC GAGT CT GAT GT TT GT CGCT GCCGC A

GC GGT T GC GGCT GAT CCT ACT CC GGT GAGC GT GGT GGGC GGGACT ATT CAT TT C GAAGGT

-continued

```
AAACTGGTTAATGCAGCCTGTGCCGTCAGCACTAAATCCGCCGATCAAACGGTGACGCTG
GGTCAATACCGTACCGCCAGCTTTACGGCGATTGGTAATACGACTGCGCAGGTGCCTTTC
TCCATCGTCCTGAATGACTGCGATCCGAAAGTGGCGGCCACCGCTGCCGTGGCTTTCTCT
GGTCAGGCAGATAACACCACCCCTAATTTGCTGGCTGTGTCCTCTGCGGACAATAGCACT
ACCGCAACCGGCGTCGGGATTGAGATTCTTGATAATACCTCTTCACCGTTGAAGCCGGAC
GGCGCGACCTTCTCGGCGAAGCAGTCGCTGGTTGAAGGCACCAATACGCTGCGTTTTACC
GCACGCTATAAGGCAACCGCCGCCGCCACGACGCCAGGCCAGGCTAATGCCGACGCCACC
TTTATCATGAAATACGAATAA-3'
``` two oligomers were chemically synthesized. They were chosen on the basis of (a) location outside of the invertible repeats that are 5' proximal and, (b) a G plus C content of approximately 50% (which relates to lysine content, Salmonella spp. having a high content of this amino acid versus Klebsiella, E. coli, etc.). Otherwise, sequences to be synthesized were arbitrarily selected and were approximately 50 bases long.

The discrete nucleotide sequences below were synthesized for testing:

5' . . . CAGGCCAGGCTAATGCCGACGCCACCTT-TATCATGAAATACGAATAAT . . . 3' (this sequence was designated ODS0098).

5' . . . CCTACTCCGGTGAGCGTGAGTGGCGG-TACTATTCATTTCGAAGGTAAACT . . . 3' (this sequence was designated ODS0100)

The synthetic oligomers were tested in colony hybridization experiments. Both probes were $^{32}$P-labelled and tested in combination, against a panel of 142 Salmonella strains obtained from the Center for Disease Control and representing all species' subgroups (1,2,3a,3b,4,5 and 6). Other organisms tested for reactivity with the probe are indicated in Table II.

TABLE II

| Target Organism* | Number tested | Hybridization Signal |
|---|---|---|
| Subgroup 1 | | |
| S. adelaide | 1 | + |
| S. agona | 3 | + |
| S. alachua | 1 | + |
| S. albany | 1 | + |
| S. anatum | 3 | + |
| S. bareilly | 2 | + |
| S. bere | 1 | + |
| S. berta | 1 | + |
| S. blockley | 1 | + |
| S. bovis-morbificans | 1 | + |
| S. braenderup | 1 | + |
| S. brandenburg | 1 | + |
| S. bredeney | 1 | + |
| S. cerro | 1 | + |
| S. chester | 1 | + |
| S. choleraesuis | 4 | + |
| S. decatur | 1 | + |
| S. derby | 1 | + |
| S. drypool | 1 | + |
| S. dublin | 3 | + |
| S. enteritidis | 5 | + |
| S. give | 1 | + |
| S. haardt | 1 | + |
| S. hadar | 3 | + |
| S. hartford | 1 | + |
| S. havana | 1 | + |
| S. heidelberg | 3 | + |
| S. indiana | 1 | + |
| S. infantis | 3 | + |
| S. inverness | 1 | + |
| S. java | 1 | + |
| S. javiana | 1 | + |
| S. johannesburg | 1 | + |
| S. kentucky | 1 | + |
| S. kottbus | 1 | + |
| S. krefeld | 1 | + |

TABLE II-continued

| Target Organism* | Number tested | Hybridization Signal |
|---|---|---|
| S. livingstone | 1 | + |
| S. london | 1 | + |
| S. madelia | 1 | + |
| S. manhattan | 1 | + |
| S. mbandaka | 1 | + |
| S. meleagridis | 1 | + |
| S. miami | 1 | + |
| S. minnesota | 1 | + |
| S. mississippi | 1 | + |
| S. montevideo | 2 | + |
| S. muenchen | 3 | + |
| S. muenster | 1 | + |
| S. new brunswick | 1 | + |
| S. newington | 1 | + |
| S. newport | 3 | + |
| S. norwich | 1 | + |
| S. ohio | 1 | + |
| S. oranienburg | 1 | + |
| S. panama | 1 | + |
| S. paratyphi A | 2 | + |
| S. paratyphi B | 1 | + |
| S. paratyphi C | 2 | + |
| S. poona | 1 | + |
| S. reading | 1 | + |
| S. rubislau | 1 | + |
| S. san diego | 2 | + |
| S. saphra | 1 | + |
| S. senftenburg | 4 | + |
| S. st. paul | 1 | + |
| S. stanley | 1 | + |
| S. sundsvall | 1 | + |
| S. tennessee | 1 | + |
| S. typhimurium | 9 | + |
| S. typhi | 2 | + |
| S. virchow | 1 | + |
| S. welterredon | 1 | + |
| S. worthington | 1 | + |
| Subgroup 2 Salmonella: | | |
| 58:dz$_{:6}$ | 1 | + |
| 30:1, z$_{28}$:z$_6$ | 1 | + |
| S. setubal | 1 | + |
| S. phoenix | 1 | + |
| Subgroup 3a Salmonella: | | |
| 62:z$_4$, z$_{23}$:- | 1 | + |
| 43$_{1,2,4}$:z$_4$,z$_{23}$:- | 1 | + |
| 18:z$_4$,z$_{32}$:- | 1 | + |
| 62:z$_{36}$:- | 1 | + |
| 48$_1$,48$_2$:z$_4$,z$_{24}$:- | 1 | + |
| Subgroup 3b Salmonella: | | |
| 65:(k):z | 1 | + |
| 61:k:1,5,(7) | 1 | + |
| 48$_{1,3,4}$:i:z | 1 | + |
| 50$_{1,2,3}$:k:z | 1 | + |
| 38:(k):Z$_{35}$ | 1 | + |
| Subgroup 4 Salmonella: | | |
| 43$_{1,3,4}$:Z$_{29}$:- | 1 | + |
| 44:z$_{36}$:- | 1 | + |
| S. wassenaar | 1 | + |

TABLE II-continued

| Target Organism* | Number tested | Hybridization Signal |
|---|---|---|
| *S. flint* | 1 | + |
| Subgroup 5 | | |
| Salmonella: | | |
| 48, 48₂₇ 48₂:2:- | 1 | − |
| *S. brookfield* | 1 | − |
| *S. marogrosso* | 1 | − |
| *S. malawi* | 1 | − |
| Subgroup 6 | | |
| Salmonella: | | |
| 11:b:1,7 | 1 | + |
| 41:b:1,7 | 1 | + |
| *S. ferlac* | 1 | + |
| *S. vrindaban* | 1 | + |
| Other genera | | |
| *E. coli* | 6 | − |
| Enteric Group 90 | 2 | − |
| *Citrobacter freundii* | 2 | + and − |
| *Enterobacter hafniae* | 1 | − |

The above strains were obtained from the CDC, Atlanta, Ga., complements of Dr. J. J. Farmer III and Alma C. McWhorter.

With some exceptions, the two probes ODS0098 and ODS0100 (a 48 mer and a 50 mer, respectively) showed excellent specificity and sensitivity. The probes reacted specifically with all Salmonella subgroups related to human pathogenesis (Subgroup 5 is a reptilean pathogen; the probes do not react with organisms from this subgroup). Of the non-Salmonella biochemically or serologically related organisms examined, only one of two *Citrobacter-freundii* cross-reacted with the probes.

To attain greater specificity, a series of shorter oligomeric probes, 17–19 bases long were examined. The discrete nucleotide sequences below were synthesized for testing:

5'-ATT GCG AGT CTG ATG TTT G-3' (this sequence was designated ODS0111)

5'-TGC AGC CTG TGC CGT CAG C-3' (this sequence was designated ODS0112)

5'-TCT GCG GAC AAT AGC ACT A-3' (this sequence was designated ODS0113)

5'-GTT GAA GGC ACC AAT AC-3' (this sequence was designated ODS0114)

5'-TGC CGT TCC CTG ACG GGA-3' (this sequence was designated ODS0115)

5'-GCG TGC GGT AAAACG CAG-3' (this sequence was designated ODS0116)

5'-CCC GAC GCC GGT TGC GG-3' (this sequence was designated ODS0117)

5'-GGC CGC CAC TTT CGG AT-3' (this sequence was designated ODS0118)

5'-GTT TGA TCG GCG GAT TT-3' (this sequence was designated ODS0119)

5'-GCT CAC CGG AGT AGG ATC-3' (this sequence was designated ODS0120)

Each of these probes were $^{32}$P-labelled and tested in colony hybridization experiments against 34 Salmonella strains, 5 Citrobacter strains, a *Enterobacter hafniae* and an *E. coli* strain. Five of the 10 probes elicited non-crossreactive hybridization patterns. However, the shorter probes sacrifice sensitivity with the concomitant gain in specificity, i.e., a small number of Salmonellae (other than subgroup 5) were non-reactive, resultant of the use of short probes.

Probes of about 30 bases in length were also tested. These probes were synthesized as 5' or 3' extensions of ODS0111, ODS0113, ODS0114, ODS0116 and ODS0119. The discrete nucleotide sequences below were tested:

5' ATT GCG AGT CTG ATG TTT GTC GCT GGC GCA-3' (this sequence was designated ODS0137)

5' GCG TGC GGT AAA ACG CAG CGT ATT GGT GCC TTC AAC-3' (this sequence was designated ODS0139)

5' TAG TGC TAT TGT CCG CAG AGG AGA CAG CCA-3' (this sequence was designated ODS0143)

5' GCC GGT TGC GGT AGT GCT ATT GTC CGC AGA-3' (this sequence was designated ODS0144)

5' ACC CAG CGT CAC CGT TTG ATC GGC GGA TTT-3' (this sequence was designated ODS0145)

5' GTA TTG GTG CCT TCA ACC AGC GAC TGC TTC-3' (this sequence was designated ODS0146)

Results of dot blot experiments employing $^{32}$P-labelled probe and pure chromosomal DNA preparations from a variety of organisms indicated that excellent specificity/sensitivity was obtained in the case of ODS0144 and ODS0146. Of the 8 Salmonella DNA preparations (representing all subgroups), only subgroup 5, the reptilean pathogen, was not detected. No cross-reactivity was seen with any DNA's from other organisms, i.e. 8 Citrobacter strains, a *Serratia marcescens*, *Morganella morganii*, *E. Coli*, *Enterobacter cloacae*, *Proteus mirabilis*, *Yersinia enterocoliticus*, *Vibrio parahemolyticus*, *Enterobacter aerogenes*, as well as 4 Shigella species, were tested and were not probe reactive.

All of the probes as described herein are highly specific probes for detecting Salmonella organisms which are pathogenic in humans. They are clinically significant in the detection of Salmonella in diarrhea specimens. Additionally, they would be useful in the detection of food-borne Salmonella, the causative agent of salmonellosis in humans.

What is claimed is:

1. A synthetic nucleic acid probe for use in detecting nucleic acid from human pathogenic microorganisms from the genus Salmonella consisting of a nucleotide sequence selected from the group consisting of:

5' GCG TGC GGT AAA ACG CAG CGT ATT GGT GCC TTC AAC-3',

5' TAG TGC TAT TGT CCG CAG AGG AGA CAG CCA-3',

5' GCC GGT TGC GGT AGT GCT ATT GTC CGC AGA-3',
5' ACC CAG CGT CAC CGT TTG ATC GGC GGA TTT-3',
5' GTA TTG GTG CCT TCA ACC AGC GAC TGC TTC-3',
5'-ATT GCG AGT CTG ATG TTT G-3',
5'-TGC AGC CTG TGC CGT CAG C-3',
5'-TCT GCG GAC AAT AGC ACT A-3',
5'-GTT GAA GGC ACC AAT AC-3',
5'-TGC CGT TCC CTG ACG GGA-3',
5'-GCG TGC GGT AAA ACG CAG-3',
5'-CCC GAC GCC GGT TGC GG-3',
5'-GGC CGC CAC TTT CGG AT-3',
5'-GTT TGA TCG GCG GAT TT-3', and
5'-GCT CAC CGG ACT AGG ATC-3';

or a nucleotide sequence fully complementary thereto.

2. A probe according to claim 1 consisting of a nucleotide sequence selected from the group consisting of 5' GCCGGTTGCGGTAGTGCTATTGTCCGCAGA 3', and
5' GTATTGGTGCCTTCAACCAGCGACTGCTTC 3'; or a nucleotide sequence fully complementary thereto.

3. The nucleic acid probe of claim 1 further consisting essentially of a detectable label.

4. The nucleic acid probe of claim 3, wherein said detectable label comprises a 3' tail nucleotide sequence having a detectable label bound thereon said 3' tail nucleotide sequence consisting of between 150 and 1000 nucleotides.

5. The probe of claim 4 wherein said detectable label is a hapten.

6. The probe of claim 5 wherein said hapten is selected from the group consisting of biotin, iminobiotin, and fluorescein.

7. A reagent for use in detecting nucleic acid from human pathogenic microorganisms from the genus Salmonella consisting essentially of at least one nucleic acid probe of claim 1 dispersed in a buffer solution.

8. A reagent according to claim 7 consisting essentially of at least one nucleic acid probe consisting of a nucleotide sequence selected from the group consisting of

```
5'-AT GAGA CAT AAA TT AAT GACCT CT ACT ATT GC GAGT CT GAT GT TTT GT CGCT GCC GCA
    GC GGT T GC GGCT GAT CCT ACT CC GGT GAGC GT GGT GGGC GGGA CT ATT CAT TT C GAA GGT
    AAA CT GGT T AAT GC AGC CT GT GCC GT CAG CACT AAA T CC GCC GAT C AAA C GGT GAC GCT G
    GGT CAAT ACC GT ACC GCC AGC T TT AC GGC GAT T GGT AAT AC GACT GC GC AGGT GCC TTT C
    T CCA T CGT CCT GAA T GACT GC GAT CC GAA AGT GGC GGC C ACC GCT GCC GT GGC T TT CT CT
    GGT CAGGC AGAT AAC ACC ACC CCT AAT TT GCT GGCT GT GT CCT CT GC GGA C AAT AGC ACT
    ACC GC AAC C GGC GT C GGGA T T GAGA T T CT T GAT AA T ACCT CT T C ACC GT T GAA GCC GGAC
    GGC GC GACCT T CT C GGC GAA GC AGT C GCT GGT T GAA GGC ACC AAT ACGCT GC GT TTT ACC
    GC ACGCT AT AAGGC AAC C GCC GC C GCC ACG ACG CC AGGCC AGGCT AAT GCC GAC GCC ACC
    TTT AT CAT GAAAT ACGAAT AA-3'
```

5' GCCGGTTGCGGTAGTGCTATTGTCCGCAGA 3', and

5' GTATTGGTGCCTTCAACCAGCGACTGCTTC 3';

or a nucleotide sequence fully complementary thereto.

9. The reagent of claim 7 further consisting essentially of a hybridization enhancer;

a detergent; and carrier DNA.

10. A method of detecting the presence of a human pathogenic microorganism from the genus Salmonella in a bacteria-containing sample comprising the steps of a) providing a sample suspected of containing a human pathogenic microorganism from the genus Salmonella;

b) denaturing the DNA of bacteria in said sample;

c) providing a synthetic nucleic acid probe consisting of a nucleotide sequence selected from the group consisting of:

5' GCG TGC GGT AAA ACG CAG CGT ATT GGT GCC TTC AAC-3',

5' TAG TGC TAT TGT CCG CAG AGG AGA CAG CCA-3',

5' GCC GGT TGC GGT AGT GCT ATT GTC CGC AGA-3',

5' ACC CAG CGT CAC CGT TTG ATC GGC GGA TTT-3',

5' GTA TTG GTG CCT TCA ACC AGC GAC TGC TTC-3',

5'-ATT GCG AGT CTG ATG TTT G-3',

5'-TGC AGC CTG TGC CGT CAG C-3',

5'-TCT GCG GAC AAT AGC ACT A-3',

5'-GTT GAA GGC ACC AAT AC-3',

5'-TGC CGT TCC CTG ACG GGA-3',

5'-GCG TGC GGT AAA ACG CAG-3',

5'-CCC GAC GCC GGT TGC GG-3',

5'-GGC CGC CAC TTT CGG AT-3',

5'-GTT TGA TCG GCG GAT TT-3', and

5'-GCT CAC CGG ACT AGG ATC-3', or a nucleotide sequence fully complementary thereto;

d) contacting said nucleic acid probe with said denatured DNA under conditions which allow said nucleic acid probe to hybridize to DNA from a human pathogenic microorganism from the genus Salmonella present in said sample; and e) detecting said hybridized nucleic acid probe thereby indicating the presence of a human pathogenic microorganism from the genus Salmonella in said sample.

11. The nucleic acid probe of claim 4, wherein said 3' tail nucleotide sequence consists of between 150 and 500 nucleotides.

12. The nucleic acid probe of claim 11, wherein said 3' tail nucleotide sequence consists of between 200 and 400 nucleotides.

13. A synthetic nucleic acid probe for use in detecting nucleic acid from human pathogenic microorganisms from the genus Salmonella consisting of:

an 18–50 nucleotide fragment of:

or a nucleotide sequence fully complementary thereto.

14. The nucleic acid probe of claim 13 further consisting essentially of a detectable label.

15. The nucleic acid probe of claim 14, wherein said detectable label comprises a 3' tail nucleotide sequence having a detectable label bound thereon, said 3' tail nucleotide sequence consisting of between 150 and 1000 nucleotides.

16. The nucleic acid probe of claim 15, wherein said 3' tail nucleotide sequence consists of between 150 and 500 nucleotides.

17. The nucleic acid probe of claim 16, wherein said 3' tail nucleotide sequence consists of between 200 and 400 nucleotides.

18. The nucleic acid probe of claim 14 wherein said detectable label is a hapten.

19. The nucleic acid probe of claim 18 wherein said hapten is selected from the group consisting of biotin, iminobiotin, and fluorescein.

20. A reagent for use in detecting nucleic acid from human pathogenic microorganisms from the genus Salmonella consisting essentially of at least one nucleic acid probe of claim 13 dispersed in a buffer solution.

21. A reagent according to claim 20 further consisting essentially of a hybridization enhancer;

a detergent; and carrier DNA.

22. A method of detecting the presence of a human pathogenic microorganism from the genus Salmonella in a bacteria-containing sample comprising the steps of a) providing a sample suspected of containing a human pathogenic microorganism from the genus Salmonella;

b) denaturing the DNA of bacteria in said sample;

c) providing a synthetic nucleic acid probe according to claim 13, d) contacting said nucleic acid probe with said denatured DNA under conditions which allow said nucleic acid probe to hybridize to DNA from a human pathogenic microorganism from the genus Salmonella present in said sample; and e) detecting said hybridized nucleic acid probe thereby indicating the presence of a human pathogenic microorganism from the genus Salmonella in said sample.

* * * * *

UNITED STATES PATENT AND TRADEMARK OFFICE
CERTIFICATE OF CORRECTION

PATENT NO. : 5,486,454
DATED : January 23, 1996
INVENTOR(S) : M. Jane Madonna and Derek Woods It is certified that error appears in the above-indentified patent and that said Letters Patent is hereby corrected as shown below:

Col. 4, line 48, after "subclones" delete the "38".

Col. 6, line 63, "hereto" should be --hetero--.

Signed and Sealed this

Tenth Day of September, 1996

Attest:

BRUCE LEHMAN

*Attesting Officer*  *Commissioner of Patents and Trademarks*